United States Patent
Leveque et al.

(10) Patent No.: US 7,402,135 B2
(45) Date of Patent: Jul. 22, 2008

(54) APPARATUS AND METHOD TO EVALUATE HYDRATION OF THE SKIN OR THE MUCOUS MEMBRANES

(75) Inventors: Jean-Luc Leveque, Paris (FR); Bernard Querleux, Le Perreux (FR); Franck Giron, Ferrieres en Brie (FR)

(73) Assignee: L'Oreal, Paris (FR)

( * ) Notice: Subject to any disclaimer, the term of this patent is extended or adjusted under 35 U.S.C. 154(b) by 36 days.

(21) Appl. No.: 10/756,274

(22) Filed: Jan. 14, 2004

(65) Prior Publication Data
US 2004/0171962 A1 Sep. 2, 2004

Related U.S. Application Data

(60) Provisional application No. 60/466,406, filed on Apr. 30, 2003.

(30) Foreign Application Priority Data

Jan. 14, 2003 (FR) .................................. 03 00367
Mar. 13, 2003 (FR) .................................. 03 03118

(51) Int. Cl.
*A61B 5/00* (2006.01)
*G01N 27/22* (2006.01)

(52) U.S. Cl. .................. 600/306; 600/300; 600/307; 73/29.04

(58) Field of Classification Search ............... 600/307, 600/306; 73/29.04
See application file for complete search history.

(56) References Cited

U.S. PATENT DOCUMENTS

| 4,066,068 A | * | 1/1978 | Nilsson et al. | 600/307 |
| 4,845,421 A | * | 7/1989 | Howarth et al. | 324/688 |
| 4,860,753 A | * | 8/1989 | Amerena | 600/306 |
| 4,966,158 A | * | 10/1990 | Honma et al. | 600/547 |
| 5,514,973 A | * | 5/1996 | Byler et al. | 324/695 |
| 5,738,107 A | * | 4/1998 | Martinsen et al. | 600/547 |
| 5,832,103 A | * | 11/1998 | Giger et al. | 382/130 |
| 5,938,593 A | * | 8/1999 | Ouellette | 600/300 |
| 5,961,471 A | * | 10/1999 | Nickson | 600/546 |

(Continued)

FOREIGN PATENT DOCUMENTS

DE 199 36 097 2/2001

(Continued)

OTHER PUBLICATIONS

"L'Oreal and St.Microelectronics Applying Semiconductors to Skin Aging", Press Releases, Oct. 22, 2002, 2 pages.

*Primary Examiner*—Robert L. Nasser, Jr.
*Assistant Examiner*—Patricia Mallari
(74) *Attorney, Agent, or Firm*—Oblon, Spivak, McClelland, Maier & Neustadt, P.C.

(57) ABSTRACT

An apparatus enabling a person to evaluate the hydration of a region of the skin or the mucous membranes. The apparatus includes a sensor including an array of non-optical detection cells and processor apparatus arranged to deliver at least one piece of information relating to the hydration of the region on the basis of signals coming from the sensor. A method for evaluation of hydration is also provided. The apparatus and method can also be used for evaluating, e.g., aging or the effectiveness of a treatment regimen.

27 Claims, 6 Drawing Sheets

U.S. PATENT DOCUMENTS

| | | | |
|---|---|---|---|
| 6,083,174 A * | 7/2000 | Brehmeier-Flick et al. | 600/561 |
| 6,370,426 B1 | 4/2002 | Campbell et al. | |
| 6,525,547 B2 * | 2/2003 | Hayes | 324/662 |
| 6,762,609 B2 * | 7/2004 | Alanen et al. | 324/686 |
| 6,944,491 B2 | 9/2005 | Leveque | |
| 6,966,877 B2 * | 11/2005 | Lahtinen | 600/307 |
| 2002/0107456 A1 | 8/2002 | Leveque | |
| 2004/0125996 A1 * | 7/2004 | Eddowes et al. | 382/128 |
| 2005/0209529 A1 | 9/2005 | Leveque | |

FOREIGN PATENT DOCUMENTS

| | | |
|---|---|---|
| EP | 1 177 766 | 2/2002 |
| EP | 1 208 539 | 5/2002 |
| EP | 1 316 912 | 6/2003 |
| FR | 2 821 541 | 9/2002 |
| JP | 2000-69154 | 3/2000 |
| JP | 2000-175871 | 6/2000 |
| JP | 2002-159474 | 6/2002 |
| JP | 2002-269211 | 9/2002 |
| JP | 2004-141259 | 5/2004 |
| WO | WO 01/24700 | 4/2001 |
| WO | WO 02/056776 | 7/2002 |
| WO | WO 02/069802 | 9/2002 |

* cited by examiner

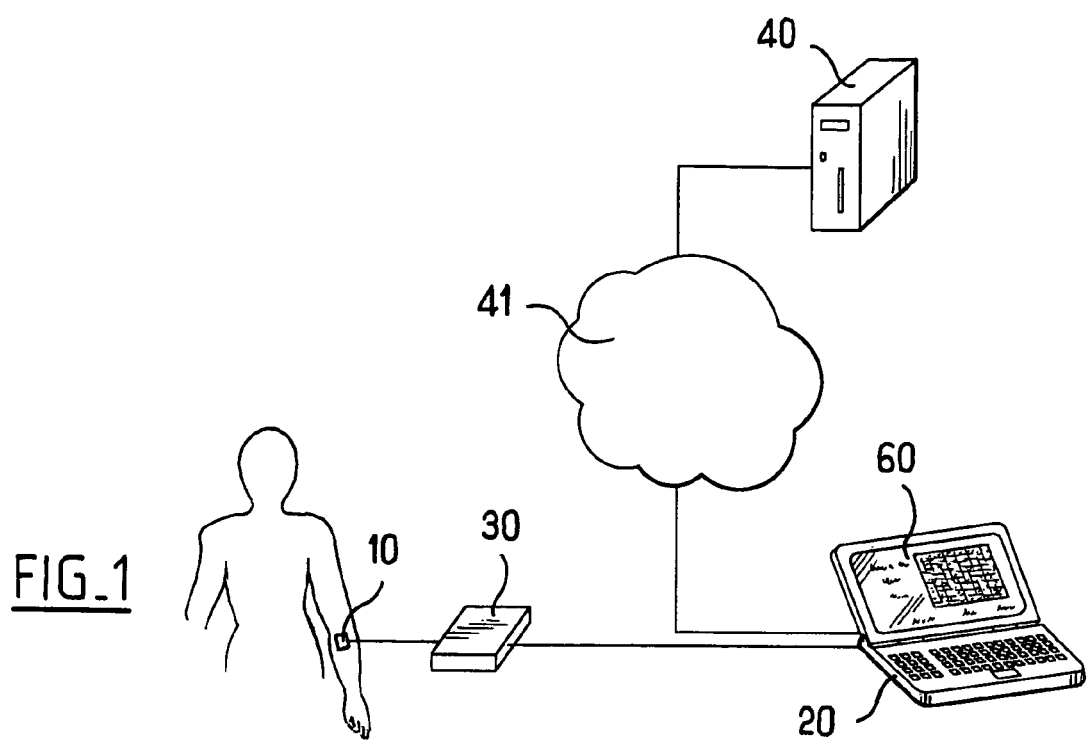
FIG_1
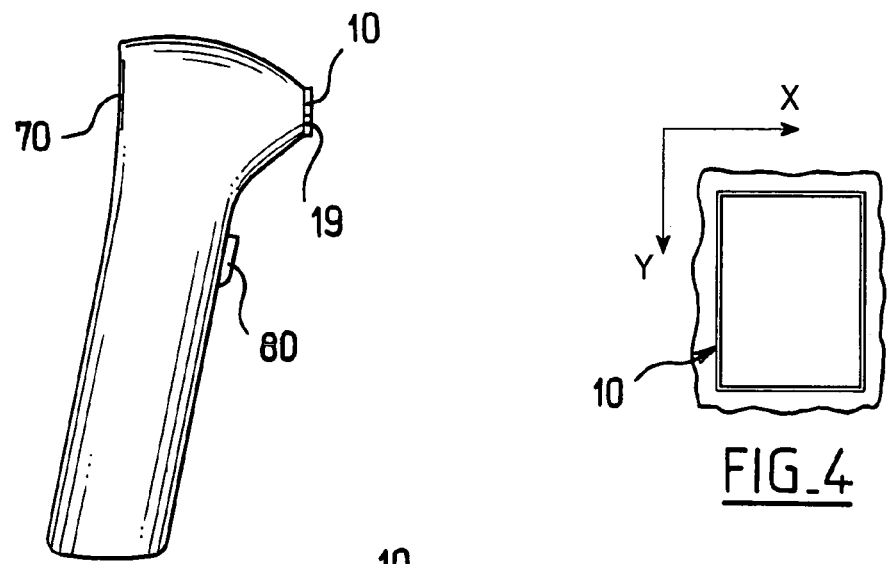
FIG_2
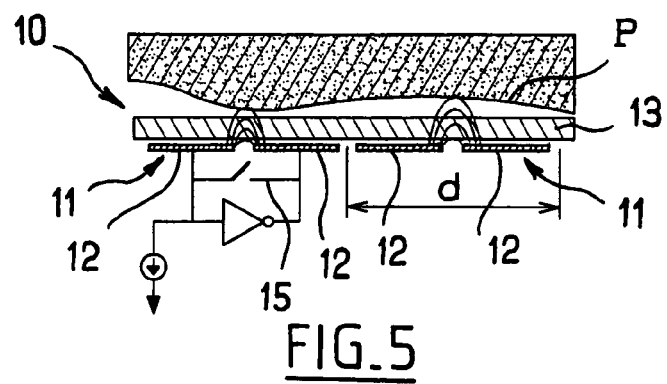
FIG_4
FIG_5

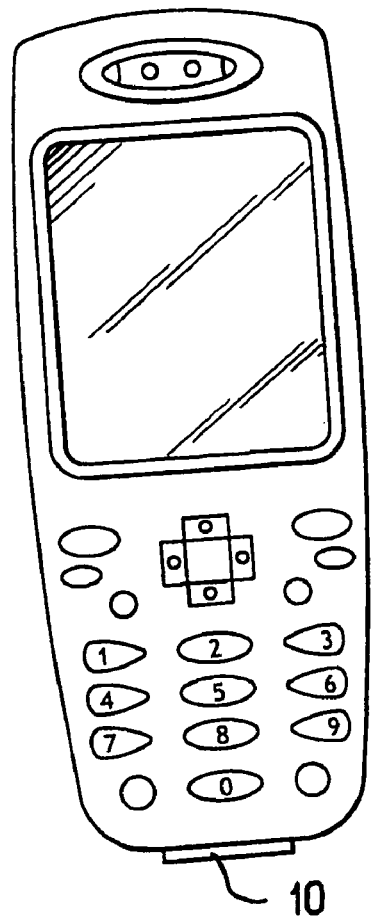
FIG_3
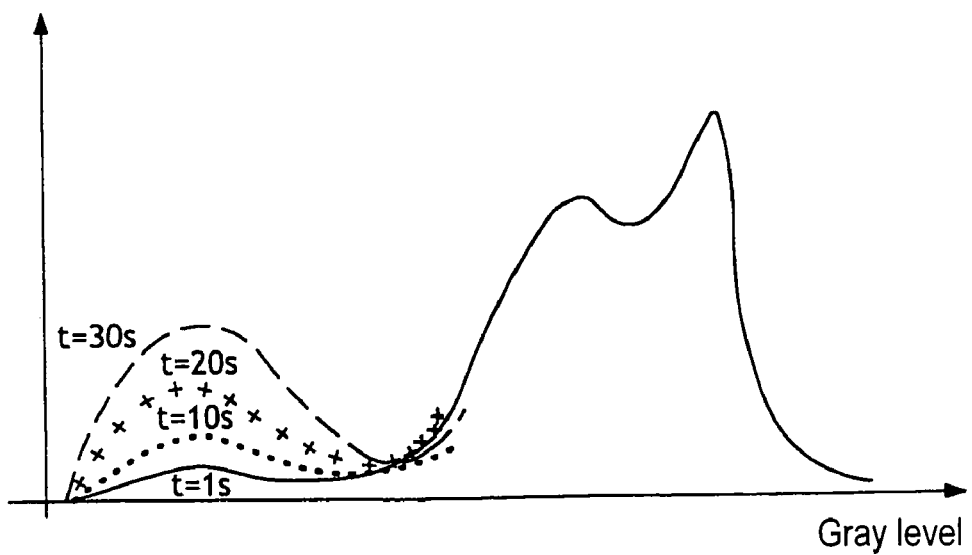
FIG_10

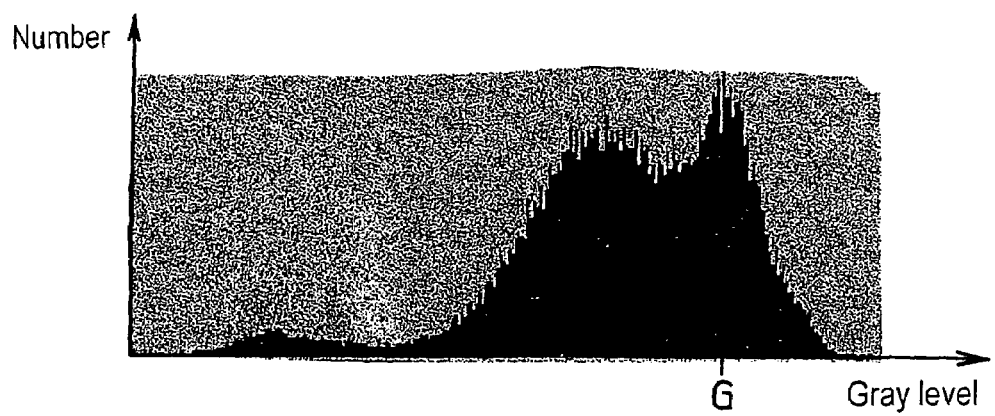
FIG_7
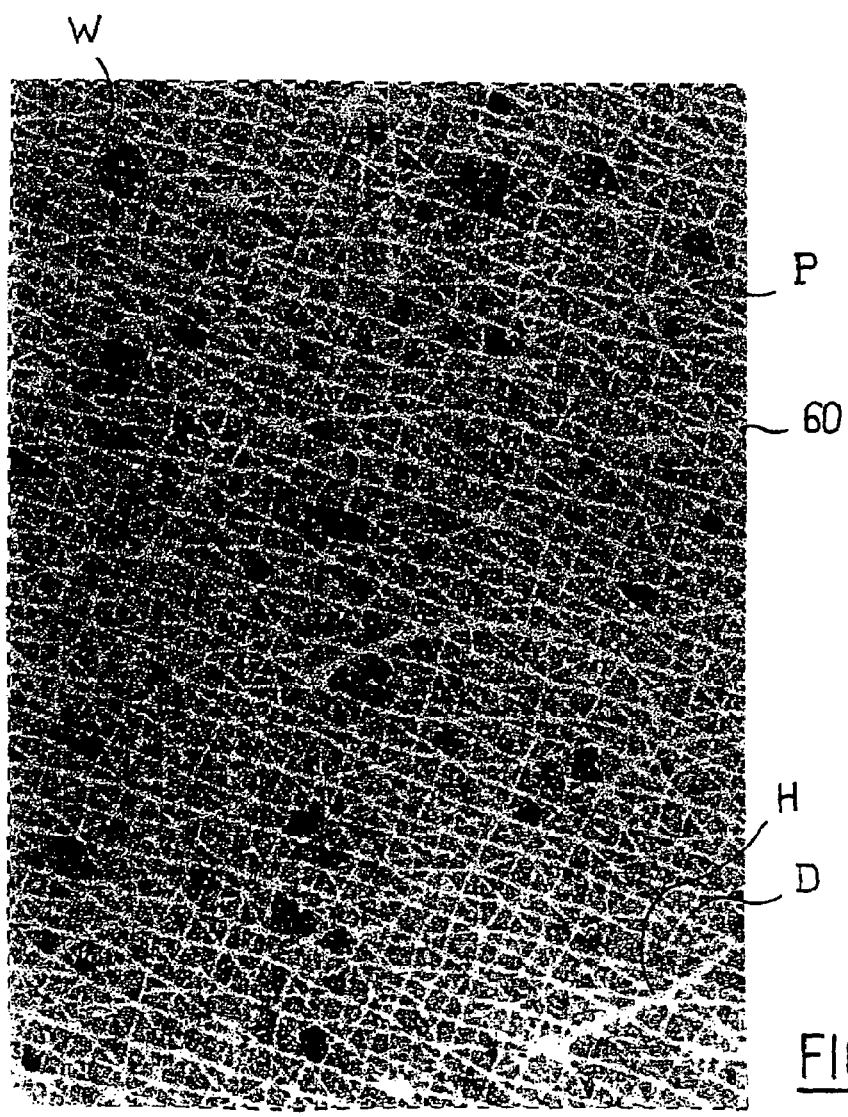
FIG_6

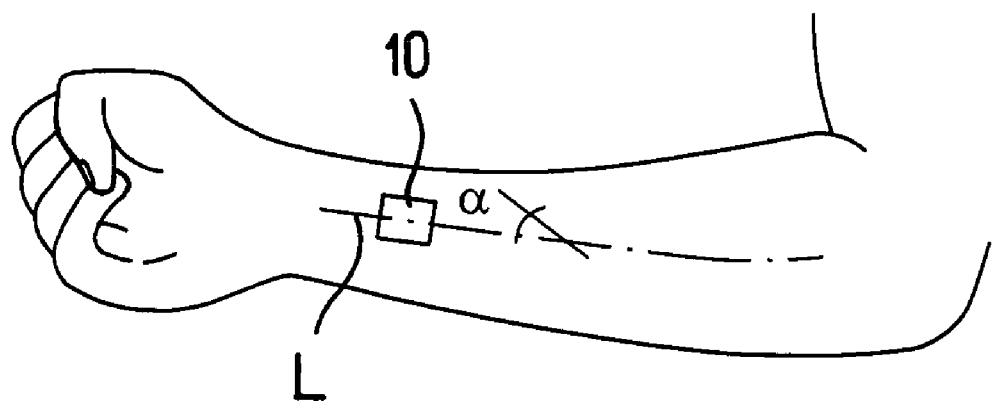
FIG_11
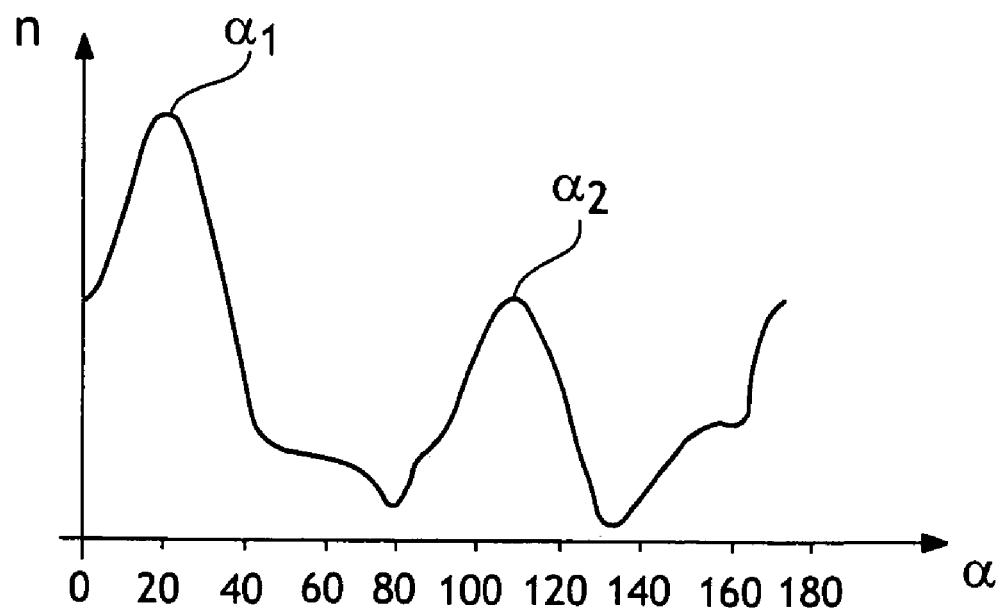
FIG_12

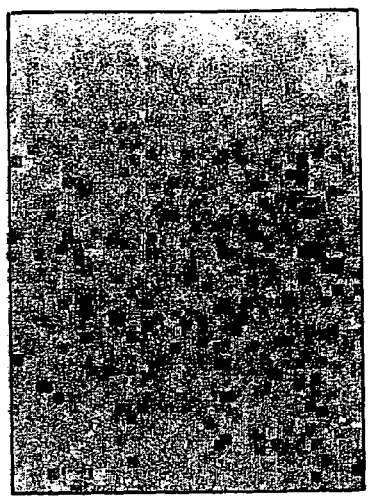
FIG_13
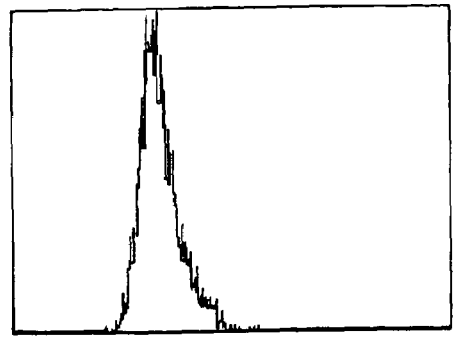
FIG_14
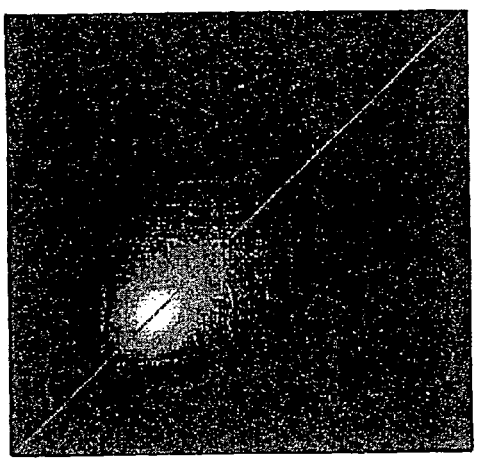
FIG_15
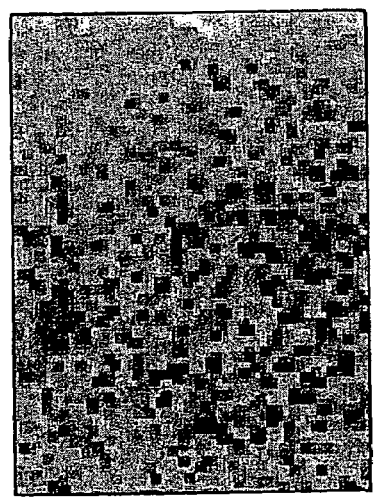
FIG_16
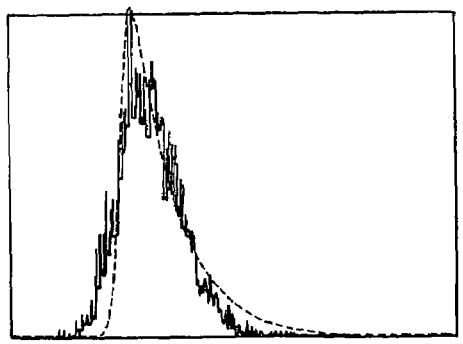
FIG_17
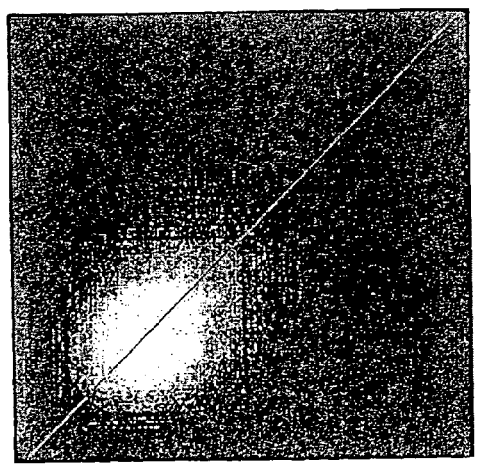
FIG_18

APPARATUS AND METHOD TO EVALUATE HYDRATION OF THE SKIN OR THE MUCOUS MEMBRANES

CROSS-REFERENCE TO RELATED APPLICATIONS

This document claims priority to French Application Numbers 03 00367, filed Jan. 14, 2003; 03 03118, filed Mar. 13, 2003 and U.S. Provisional Application No. 60/466,406, filed Apr. 30, 2003, the entire contents of which are hereby incorporated by reference.

BACKGROUND OF THE INVENTION

1. Field of the Invention

The present invention relates to methods and apparatuses seeking to evaluate hydration of the skin and/or the mucous membranes. The invention is particularly advantageous for evaluation of the lips.

2. Discussion of Background

The term "hydration" designates the water content in the skin and on its surface, including water that comes from transpiration.

U.S. Pat. No. 6,370,426 describes an apparatus for measuring hydration of the human skin. The apparatus includes means for measuring variation in impedance between two electrodes in electrical contact with the skin. Patent application WO 02/056766 also describes an apparatus that is quite similar.

The German supplier Courage & Khazaka sells a corneometer under the reference CM825® for measuring the capacitance of the stratum corneum. The measurement is based on the difference in dielectric constants that exists between water and other substances present in the skin, thereby establishing a relationship between capacitance and the proportion of water in the surface layers of the skin.

Proposals are made in patent application EP 1,177,766 and U.S. counterpart application 2002/0107456 to use a sensor including an array of non-optical detection cells, in particular capacitive cells, for obtaining information concerning the microrelief of a non-dermatoglyphic region of the human body, for example the surface density of skin lines, the anisotropy coefficient of the density of said lines, and the number and size of pores in the skin.

Applications WO 01/24700 and DE 199 36 097 describe devices and methods of authentication by fingerprint analysis.

Application WO 01/24700 describes analyzing possible variation, due to perspiration, of the image acquired by means of a sensor so as to confirm to the authentication system that the finger whose imprint is being analyzed is indeed alive.

DE 199 36 097 describes adjusting a sensitivity threshold in fingerprint recognition as a function of skin moisture.

The above documents relate to methods and apparatus which do not seek to deliver information relating to skin hydration in a form that can be understood directly by an individual, in order to inform the individual about the state of the skin.

SUMMARY OF THE INVENTION

The present invention provides an advantageous apparatus enabling at least one item of information to be delivered relating to the hydration of a region of the skin or the mucous membranes.

In one exemplary embodiment, the apparatus includes a sensor that includes an array of non-optical detection cells, preferably capacitive detection cells, and a processor apparatus arranged to deliver the above information on the basis of signals coming from the sensor. The information may be delivered by the apparatus in a form of intelligible information, i.e., information that can be understood directly by an individual, e.g., a sound and/or visual message. The visual message can be, for example, a printed message or a screen display. Such a message may include, by way of example, a note or a qualifier such as "skin sufficiently hydrated," "skin insufficiently hydrated," or even other terms.

The signals coming from the sensor may be analog or digital. By way of example, the sensor can in particular, deliver a value encoded on some number of bits, e.g. 8 bits, associated with each detection cell.

According to one of the advantageous aspects, signals can be delivered by the sensor which are representative of the hydration of the examined region.

Advantageously, the sensor used preferably can present spatial resolution of better than 100 micrometers ($\mu$m), more preferably equal to or better than 50 $\mu$m, in at least one direction, and preferably in two orthogonal directions of a plane. By way of example, the sensor can include more than 200×200 detection cells, and the array of detection cells can occupy an area lying in the range, for example, of 10 millimeters (mm)×10 mm to 20 mm×20 mm. The array of cells in the sensor is advantageously two-dimensional, with each cell preferably being individually addressable.

In an exemplary embodiment, the apparatus of the invention can be arranged to deliver at least one image of the region analyzed by the sensor, with the gray level of each pixel of the image being representative of the capacitance measured by the detection cell. A gray level of 0 corresponds, for example, to black on the image and a maximum gray level, e.g. equal to 255 when using 8-bit coding, corresponds to white, with the gray levels between these extreme values corresponding to various respective intermediate shades.

The apparatus can be arranged to deliver and analyze a succession of images of the same region of the skin or the mucous membranes, for example in order to evaluate transpiration, as described in detail below.

The processor apparatus can perform a statistical processing of the image, and the information can be the result of the statistical processing, and optionally additional information or data. Where appropriate, the information which is delivered can be obtained after comparing the sorted results of the processing of the image with other data, e.g., concerning the age, the sex, and the ethnic type of the person concerned. The statistical processing can include analyzing the gray levels of the image. For example, the gray level shared by the greatest number of pixels in the image can be determined or analyzed. Further, by way of example, the statistical processing can include calculating the mean gray level of the image or at least of a portion thereof.

In accordance with one example or variant implementation of the invention, the statistical processing includes establishing at least one co-occurrence matrix. The matrix can be determined on the basis of an image processed by erosion and resampling. The uniformity of hydration may be determined at least on the basis of knowledge of the co-occurrence matrix, for example, with the area of the co-occurrence matrix considered as being representative of the uniformity of hydration. The use of a co-occurrence matrix makes it possible, at least to some extent, to take account of the relative positioning of zones that are dark in the image relative to zones that are pale.

The statistical processing can also include subdividing the image into subsets of given size, calculating a mean gray level for each subset, and calculating the variance between these mean gray levels. The variance can also be calculated for different sizes of subsets, and the size for which the variance is at a maximum may be determined. This size can be considered as representative of the size of non-uniformities in the image.

The information delivered can include an indication relating to the uniformity of hydration. By way of example, non-uniformity of hydration can be representative of droplets of sweat existing on the surface of the skin. Non-uniformity of hydration can also be associated with the existence of spots due to photo-aging, for example.

In order to evaluate the non-uniformity of hydration, the invention can determine, for example, the mean gray levels of preferably non-intersecting subsets of the image and calculate a value representative of a difference between these mean gray levels, e.g., the standard deviation.

The various subsets can be distributed in various ways within the image, for example they may be formed by subdividing at least a portion of the image into a rectangular grid. The subsets may also be disposed on the image in an irregular manner, at locations selected on the image, e.g., as a function of a particular value of gray level at the locations, for example, gray levels lying within specific ranges. The subsets can be localized on the image in such a manner that the corresponding mean gray levels include extreme values presenting significant differences, for example.

The processor apparatus can compare the image with a bank of images and, at least on the basis of the comparison, to extract therefrom information that is useful for evaluating the state of the skin or the mucous membranes. This bank of images can be accessed, where appropriate, via a computer or a telephone network.

The processor apparatus can be arranged so that the sensor analyzes the region for a predefined duration, which can be short. This duration may lie in the range for example of 1 second (s) to 30 s, for example, and in particular in the range 2 s to 10 s, or further by way of example in the range 3 s to 7 s. When it is desired to observe how hydration varies over time, the duration may be longer than when it is desired merely to measure hydration at a given instant.

The processor apparatus can also deliver an indication relating to the state of aging of the skin. In an exemplary embodiment, the processor apparatus can determine two major directions of skin lines relative to the axis of the arm, for example, together with a difference that exists between these directions and, on the basis of at least of this difference, to deliver an indication relating to the state of aging of the skin. According to one of the advantageous aspects of the invention, it has been recognized that this difference is generally a function of the ages of individuals, and decreases with increasing age, and therefore, the apparatus can provide information concerning aging based on this difference. The term "skin lines" is used to designate the lines formed by the furrows that extend between the plateaux of the skin.

The apparatus can be arranged to exchange data over a wired or wireless link with a personal computer or a portable terminal, in particular a portable telephone or a personal digital assistant (PDA).

Where appropriate, the apparatus may include at least one second sensor of some other type, including, for example, a biosensor or sensor of conductivity, temperature, color, elasticity, or pH.

In another of its aspects, the invention also provides a method of evaluating the hydration of a region of the skin or the mucous membranes. The method includes the following steps:
  applying to the region a sensor including an array of non-optical detection cells, preferably capacitive detection cells; and
  picking up signals coming from the sensor and, on the basis of the signals, delivering information relating to the hydration of said region, and possibly also to its aging.

The method can include issuing a message containing the information, with such a message being a sound and/or visual message, for example, in particular a printed message or a screen display. The message can include numbers, letters, words, or any other intelligible element. Prior to applying the sensor to the skin, the skin can be cleaned and/or dried by means of an absorbent material in order to avoid any initial presence of droplets of sweat, for example.

On the basis of the signals delivered by the sensor, it is also possible to determine hydration non-uniformity, and in particular to evaluate the amount of transpiration as a function of the non-uniformity, where transpiration gives rise to hydration that is non-uniform, associated with the local appearance of droplets of sweat. It may also be useful to study hydration uniformity, where appropriate, to obtain information relating to photo-aging of the skin, for example.

Information relating to the hydration or the aging of the region can be obtained by performing at least one kind of statistical processing on at least one image obtained using the sensor. The image can be displayed on a screen or it may be printed, however it is also possible for the image not to be displayed and, where appropriate, it may be recorded on a data medium such as a hard disk or an optical disk, for example.

As mentioned above, the region can be analyzed with the sensor for a predetermined duration, of shorter or longer extent depending on whether it is desired to evaluate hydration at a given instant or to track variation thereof in time, e.g., for the purpose of quantifying transpiration.

On the basis of the signals coming from the sensor, it is also possible to provide an indication relating to the density of pores in the skin and/or their size.

On the basis of the signals delivered by the sensor, it is also possible to determine two major directions of skin lines and to calculate a difference between the directions. Knowledge of such a difference can be useful in evaluating the aging of the skin.

The results of two evaluations relating to the hydration of the region at two different instants can be compared to deliver an indication associated with the variation of hydration between those two instants. By way of example, this can enable the individual who is the subject of the evaluations to be informed about the effect of a treatment. By way of example, hydration of a region of the skin or of the mucous membranes may be evaluated at a first instant, treatment may be performed to hydrate the region, e.g. by applying a moisturizing cream, and then a second evaluation can be performed at a subsequent instant, e.g. several hours or days later in order to determine the effect of the treatment.

By way of example, it is also possible to evaluate transpiration at a first instant, to perform treatment seeking to reduce transpiration, e.g., by applying a deodorant, and then to perform a second evaluation at a subsequent instant, and deduce information relating to the effectiveness of the treatment by comparing the evaluations.

It is also possible to evaluate the hydration of a region of the body that is not exposed to a given environment, for example, that is not exposed to the sun, and to evaluate a region of the body that is exposed to the environment. The results can then be compared to provide information that is of use in evaluating the incidence of the environment on the region, and where appropriate on the aging of the skin, for example.

It is also possible to analyze the region with the sensor in a first geographical location, for example, in a beauty parlor, at a point-of-sale, or at home, and to transmit the data obtained by the sensor remotely over a network such as the Internet, an Intranet, or a mobile telephone network, and then process the data in a second geographical location, e.g., a research center, for the purpose of evaluating the hydration of the region.

The result of the evaluation can be transmitted over a network such as the Internet, an Intranet, or a mobile telephone network. It is also possible to transmit the result of the evaluation by post. The result of the evaluation can be accompanied, where appropriate, with a prescription for a product having an action on the hydration of said region, e.g., an antiperspirant or a moisturizer.

In accordance with one example, for acquisition of data, the sensor can be applied to a non-dermatoglyphic region of the body, and in particular to the forearm.

In an implementation of the invention, images of the region under study are obtained successively in time by the sensor and are stored, and/or information relating to the hydration state and/or to the uniformity of hydration is stored. Images may be stored, for example, for the purpose of comparing them. With this information, it is possible in deferred or elapsed time, for example, to compare at least two values obtained by processing two successive images in order to reveal improvement or deterioration in the state of the skin over time, for example, with respect to its hydration, or evaluate transpiration.

In accordance with yet another aspect, the invention provides a method of prescribing a product, such as a cosmetic product. The method may include the following steps:

evaluating the hydration of a region of the skin or the mucous membranes by implementing a method as defined above; and in the light of the result of the evaluation, prescribing a cosmetic having an effect on the hydration of the region.

The term "cosmetic" is used to designate a product as defined in EEC Council Directive 93/35/EEC of Jun. 14, 1993. Body or face lotions and creams for moisturizing the skin are examples of cosmetics, as are antiperspirants.

In accordance with another aspect, the invention also provides a method of determining the effectiveness of treatments with respect to the hydration of the skin. The method includes the following steps:

performing a first evaluation of skin hydration;

performing the treatment;

after the treatment, performing a second evaluation of the hydration of the region; and wherein at least one of the first and second evaluations being performed by implementing a method as defined above. Preferably, the two evaluations are performed by implementing the same method.

In accordance with a further aspect, the invention also provides a method of treating a region of the body. The method includes:

evaluating the hydration of the region by implementing the method as defined above; and performing a treatment that has action on the hydration of the skin in the light of the result of the evaluation. The treatment can be performed by a topical, oral, or other technique. The treatment can also include complying with a particular diet or training regimen or administering specific kinds of care, such as massaging.

In accordance with yet another aspect, the invention provides a method of promoting the sale of a product, in particular a cosmetic. In accordance with this aspect, the activity or effectiveness of the product is demonstrated as revealed by apparatus or a method as defined above. Such product promotion can be performed using any communications channel. In particular, it may be performed by a sales person, directly at a point-of-sale, by radio, television, or telephone, in particular in the form of advertising spots or short messages. It may also be performed by means of written press or by any other document, in particular for advertising purposes. It may also be performed over the Internet, or over any other suitable computer network or over a mobile telephone network. It may also be performed directly on the product, in particular on its packaging or on instructions associated therewith.

The invention also provides the use of a fingerprint sensor having an array of capacitive detection cells integrated in a microcomputer or a portable terminal for evaluating skin hydration.

In accordance with a still further aspect, the invention also provides a mobile telephone fitted with a sensor including an array of capacitive detection cells for application to a region of the skin or the mucous membranes, with the telephone being arranged to process the signals delivered by the sensors in order to provide information relating to the hydration of the skin or the mucous membranes. By way of example, the information can be delivered in the form of a sound and/or visual message or by sending a "Short Message Service" or a "Multimedia Messaging Service" type file to a data processing center which in return delivers a sound and/or visual message, for example, a printed message or a screen display.

BRIEF DESCRIPTION OF THE DRAWINGS

Other characteristics and advantages of the invention will become apparent from the following detailed description, particularly when considered in conjunction with the drawings in which:

FIG. 1 is a diagram showing an example of apparatus in accordance with the invention;

FIG. 2 shows a variant of the apparatus in the form of a portable appliance;

FIG. 3 is a diagram showing a mobile telephone fitted with a sensor comprising an array of non-optical detection cells;

FIG. 4 is a fragmentary and diagrammatic front view of an example of a sensor;

FIG. 5 is a diagrammatic and fragmentary section view of two detection cells of the sensor;

FIG. 6 is an example of an image that can be obtained with the sensor of FIG. 4;

FIG. 7 is an example of a gray-level histogram;

FIG. 10 is a diagrammatic and fragmentary illustration of an example of one way in which a histogram can vary over time;

FIG. 11 shows the sensor positioned on a forearm;

FIG. 12 shows an example of how skin line directions can be distributed relative to the longitudinal axis of the arm;

FIG. 13 shows an image after erosion;

FIG. 14 is a histogram of the gray levels in the image of FIG. 13.

FIG. 15 shows the co-occurrence matrix obtained from the image of FIG. 13 after resampling; and FIGS. 16 to 18 are views analogous to FIGS. 13 to 15 respectively, obtained from a different starting image.

DETAILED DESCRIPTION OF THE PREFERRED EMBODIMENTS

Figure 9:
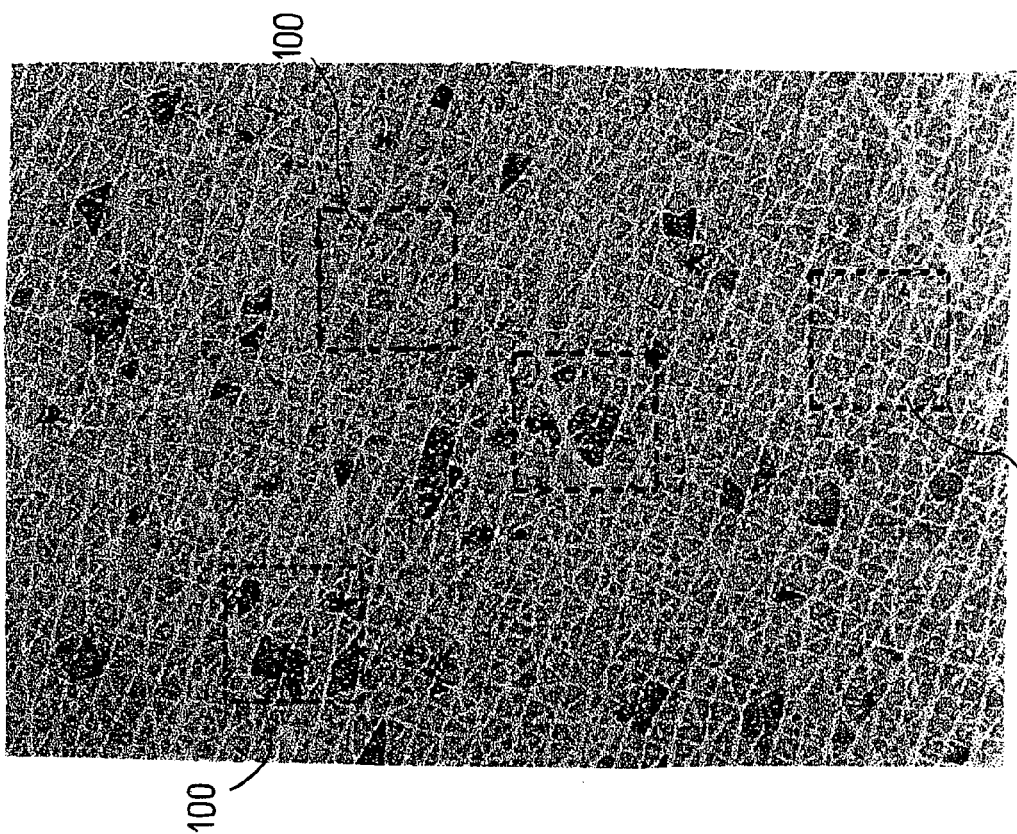
FIG. 9 shows another example of how individual zones can be defined.

FIG. 1 shows an example of an apparatus of the invention. The apparatus includes a sensor 10 for analyzing a region of the skin or the mucous membranes and processor means for processing the signals delivered by the sensor 10. The processor means can include a conventional microcomputer 20, for example, and possibly also an interface 30 enabling data from the sensor 10 to be transferred to the microcomputer 20. Where appropriate, the microcomputer can be connected to a remote server 40 via a computer network 41, e.g. the Internet or an Intranet. It is to be understood that other suitable computer or processing arrangements could be utilized.

In the example shown, the interface 30 is shown as being in the form of a unit that is distinct from the sensor 10 and from the microcomputer 20, however in accordance with the present invention the interface 30 could also be integrated in or with the sensor 10 or the microcomputer 20.

As noted above, the microcomputer 20 is merely one example of processor means that can be used. By way of a further example, in the arrangement of the invention shown in FIG. 2, the apparatus for evaluating hydration is in the form of a handheld portable appliance. This appliance can include the sensor 10, a screen or display 70 and, for example, a push-button 80 for triggering a data acquisition cycle.

Optionally where appropriate or desired, the sensor 10, whether in the embodiment of FIG. 1 or in the embodiment of FIG. 2, can be associated with at least one auxiliary sensor 19 for sensing, e.g., pH, temperature, elasticity, or color, with the information relating to hydration coming from the sensor 10 optionally being combined with other information coming from the auxiliary sensor(s) in order to obtain a better assessment of the state of the skin.

The microcomputer 20 in the example of FIG. 1 may be replaced by a portable terminal, for example a mobile telephone or a PDA.

The sensor 10 may optionally be integrated in the microcomputer 20 or the telephone or the PDA and serve also to identify the user. FIG. 3 illustrates a mobile telephone in which the sensor 10 is integrated, for example, at one end or on one side of its housing so as to make it easier to apply the sensor 10 to the forearm, for example.

In another variant, the interface 30 can be arranged to be connectable to the computer network 41 and to transmit data coming from the sensor 10 directly to the server 40 which in turn is arranged to process the data.

The sensor 10 which is shown more particularly in FIGS. 4 and 5 preferably includes a two-dimensional array of capacitive detection cells 11 extending in a plane XY.

By way of example, the sensor 10 can be a sensor sold under the trademark Touchchip® by the supplier ST-Microelectronics.

Each detection cell 11 includes two adjacent metal plates 12 which are separated from the analyzed region, e.g., the skin P, by a protective coating 13 of electrically insulating material. Electric field lines extend through the coating 13 between the plates 12, and when the skin P is in contact with the coating 13 and is situated close to the plates 12, the microrelief of the skin P interferes with the field lines and modifies the capacitance of the capacitor formed by the two plates 12.

In the above-specified Touchchip® sensor, the detection cells 11 operate in two stages. In an initial stage, the two plates 12 are interconnected by an electronic switch 15 for initialization purposes, and then in a detection stage, the switch 15 is opened and capacitance is detected. This capacitance depends in particular on the microrelief of the skin P and on the dielectric constant thereof.

By way of example, the signals delivered by the sensor 10 can be in the form of digital data, with the sensor 10 being capable of including an analog-to-digital converter (ADC). A value representing the capacitance measured by a detection cell 11, also referred to as a pixel, can be read or stored at a particular address by using addressing of the random access memory (RAM) type. The dimension d of the detection cell 11 can be less than 50 µm, and the resolution of the image can be better than 500 dots per inch (dpi).

In the example under consideration, the sensor 10 includes an array of 256×360 cells, giving an active area with dimensions of 18 mm×12.8 mm.

The sensor 10 serves to obtain an image 60 of the region under analysis. This image can be displayed, where appropriate and as shown in FIG. 1, on the screen of the microcomputer 20 or on the screen of the portable telephone shown in FIG. 3. The displayed image can be magnified, for example, by a factor of 2 or more, and further by way of example, by a factor of 6, or higher. However, it is also to be understood that, in accordance with the invention, an image need not be displayed.

The information delivered by the sensor 10 relating to each pixel of the image is in the form of a digital value encoded on 8 bits, for example, and represents the amplitude of variation in capacitance as detected locally. The image 60 can include a gray scale of levels lying in the range 0 to 255 in this example.

In accordance with the invention, it has been recognized that these gray levels are representative of the state of hydration of the region of the skin or the mucous membranes being analyzed by the sensor 10, so that the sensor 10 can serve to make a map of the hydration of the stratum corneum.

FIG. 6 shows an example of an image 60. In this figure, there can be seen skin lines D, pores T, hairs H, and spots W due to the presence of droplets of sweat.

FIG. 7 is a histogram of the gray levels in the image as a function of the number of pixels.

A correlation can be demonstrated between the gray level G shared by the largest number of pixels and hydration as measured using a conventional corneometer, e.g. a CM825®, thus making calibration possible, where appropriate.

Instead of determining which gray level is shared by the greatest number of pixels, it is also possible to calculate the mean gray level of the pixels in the image, for example.

The apparatus can be arranged in such a manner that the duration during which the sensor 10 analyzes the region of the skin is predefined, being equal to 5 seconds, for example. The duration can also be longer, as described in detail below, for example in order to quantify transpiration.

The capacitance image delivered by the sensor 10 also serves to determine the degree of uniformity of hydration.

In a first approach, it can be assumed that the standard deviation between the gray levels of specific portions of the image obtained by means of the sensor 10 is representative of the uniformity of hydration.

More precisely, in order to evaluate non-uniformity, it is possible, for example, to subdivide the image or a portion of the image into subsets 100 each comprising 500 to 1500 pixels, for example, e.g. 1024 pixels for squares having a side of 32 pixels.

Figure 8:
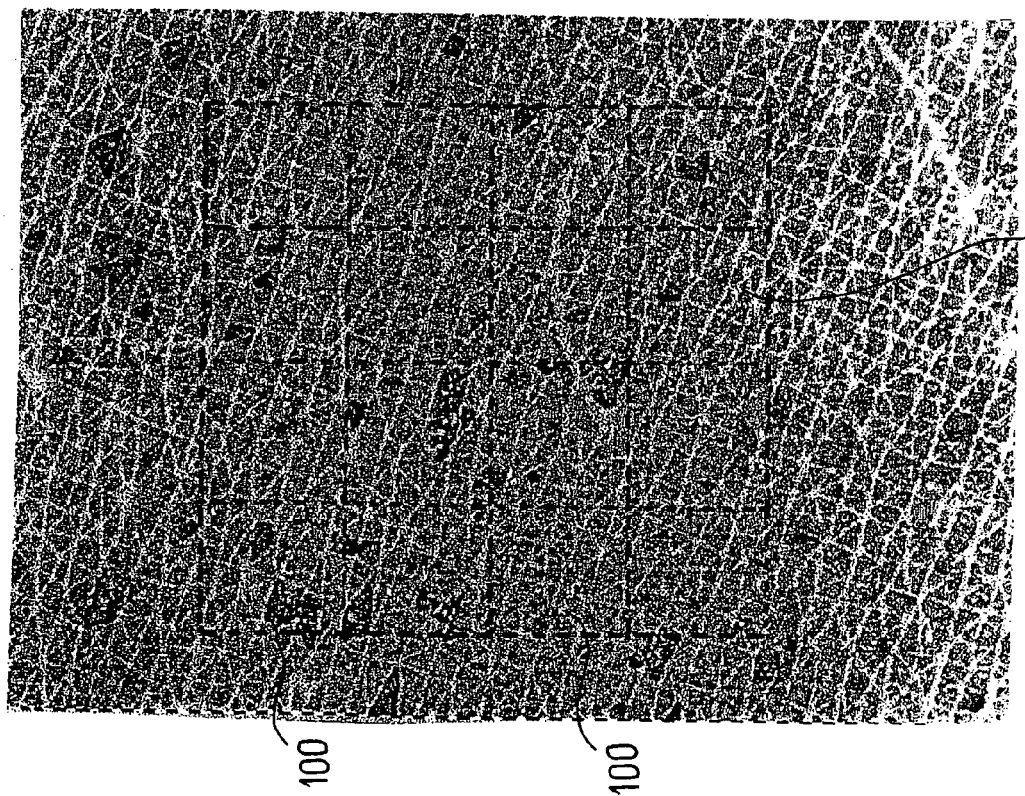
FIG. 8 illustrates an example of one way of defining individual zones in order to evaluate non-uniformity of hydration.

These subsets 100 can be disposed on the image 60 in a regular manner as shown in FIG. 8, or otherwise as shown in FIG. 9.

In FIG. 8, the subsets 100 are defined by a rectangular grid in the image 60.

For each subset 100, the mean gray level of the pixels constituting the subset is calculated.

A set of values is thus obtained from which it is possible to calculate the standard deviation. This standard deviation is representative of the non-uniformity of the image.

The non-uniformity of the image can be determined for subsets 100 of different sizes, e.g. for at least four different sizes. It is thus possible to determine the non-uniformity for subsets 100 comprising, for example, 30×30 pixels, and then for subsets 100 comprising 20×20 pixels, 10×10 pixels, and 5×5 pixels.

A maximum standard deviation is then obtained for some given size of subset 100, and the size in question can provide additional information about the uniformity of hydration, with the maximum standard deviation being representative of the mean size of hydration non-uniformities.

In FIG. 9, the locations of the subsets 100 are determined so as to obtain great disparity between the mean values of the gray levels corresponding to the subsets 100. By way of example, these subsets may be located above all in the palest zones and the darkest zones of the image. Further by way of example, a subset 100 may be positioned firstly in zones of the image that include at least some minimum number of spots W associated with transpiration, e.g., at least two, and secondly in zones that do not include any such spots or features under consideration.

In a second approach, it is possible to proceed as described below in order to evaluate hydration uniformity.

Where appropriate, it is also possible to begin by defining within the image acquired by the sensor a zone that excludes the edges of the image in order to take account of the non-uniformity with which the sensor can be pressed against the skin in such edge regions.

Thereafter, the image can be processed so as to eliminate skin lines by erosion. By way of example, it is possible to use the gray morphology erode function of the Imaq Vision Builder image processing platform from National Instruments. During erosion processing, the pixels of the image are transformed into blocks. It is possible to select an erosion matrix in the form of a square including 7×7 pixels.

FIG. 13 and FIG. 16 are images as obtained after such erosion treatment. The advantage of performing erosion treatment is that it makes it possible, when assessing hydration uniformity, to avoid taking account of zones of the skin that are not in contact with the sensor.

Thereafter it is possible to retain only one pixel per matrix, i.e. to perform resampling.

This produces an image including a relatively small number of pixels.

This image can be processed in order to provide the histogram of gray levels, i.e. with gray levels lying in the range 0 to 255 being plotted along the abscissa and with the number of pixels having each gray level corresponding to a particular position along the abscissa being plotted up the ordinate.

It is also possible from such an image to construct a co-occurrence matrix. To construct a co-occurrence matrix, pixel blocks are extracted from the image that are spaced apart by a certain distance on the image in a given direction. By way of example, this direction can be vertical in the image and the distance can correspond to 5 pixels. For a pair of pixels having respective gray levels i and j, a point is plotted having abscissa value i and ordinate value j. This is repeated for all of the pixels of the image. The resulting matrix is symmetrical about the line X=Y.

FIGS. 15 and 18 show co-occurrence matrices corresponding to different starting images. The area of the matrix increases with increasing non-uniformity in the image. Thus, for the matrices of FIGS. 15 and 18, the areas are respectively 2030 and 4640.

An advantage of co-occurrence matrix processing is that it makes it possible to select the scale on which variations are analyzed by adjusting the inter-pixel distance. For example, it is possible to ensure that the incidence of very small scale variations in gray level value on the final result is reduced since such variations do not necessarily convey information about the uniformity of hydration.

The capacitance image may also serve to reveal spots corresponding to zones that are keratotic to a greater or lesser extent, which may be the result of photo-exposure.

The apparatus of the invention can also provide a sequence of images to be acquired at predefined time intervals, with the histogram or the complete image being recorded for each image of the sequence, for example.

FIG. 10 shows an example of how low gray levels vary in a histogram over time while the sensor 10 is left on the skin. It can be observed that the number of pixels corresponding to low gray levels tends to increase over time, which can be explained by transpiration continuing throughout the observation, thereby tending to enlarge the spots W in the image, and/or to increase the number of such spots. Transpiration may be facilitated by the presence of the sensor 10 which is of occlusive character.

Comparing two histogram sequences before and after treatment seeking to reduce transpiration can serve, for example, to verify that the treatment is effective.

A histogram sequence may be processed, in order to determine the rate at which low gray levels pixels increase, for example. As a function of this rate, it is possible to determine whether the subject has a tendency to transpire or not, and to recommend a product or a treatment as appropriate, for example. By comparing the rate measured before and after treatment, it is also possible to determine the incidence of the treatment on transpiration.

The data delivered by the sensor 10 may be processed so as to provide information other than information relating purely to the hydration of the region being analyzed, for example information concerning the microrelief of the skin, in particular the number and size of the pores of the skin and the density per unit area of skin lines or the anisotropy coefficient of the skin line density.

On this topic, reference may usefully be made to European patent application EP 1,177,766 and U.S. counterpart application 2002/0107456 in the name of the present Applicant, the contents of which are incorporated herein by reference.

The anisotropy coefficient of the skin line density corresponds to the ratio of the density of lines D surrounding the plateaus of the skin in a first direction to the density in a second direction perpendicular to the first. This ratio varies with age and enables information to be obtained concerning the aging state of the skin, for example.

It is also possible to process the image so as to determine two directions in which skin lines extend for the most part. In this case the image can be obtained using a sensor including an array of capacitive detection cells, but other types of sensor having non-optical detection cells can also be used, e.g. cells measuring temperature or conductivity.

In order to determine the major directions of the skin lines, it is possible to proceed as follows, for example.

The sensor 10 is initially placed on the central face of the forearm, for example, with the long side of the sensor 10 parallel to the longitudinal axis L of the arm, as shown in FIG. 11.

An image can then be acquired whose size in pixels is 256×360, for example. A circular region of interest is defined in the image having a diameter of 248 pixels, for example.

A first pre-processing step is then performed to cancel spatial non-uniformities in low signal levels, in particular, due to non-uniform contact over the entire acquisition area.

Thereafter, the number of gray levels is reduced from 256 to 5, e.g. by using a dynamic cluster algorithm which consists in distributing the gray levels amongst 5 levels providing the greatest amount of information about the image.

On the 5-level image, a "co-occurrence" method is used by searching, in a fixed study direction, for a mean pattern in the displayed image. The method is repeated after varying the angle α between the study direction and the longitudinal axis L.

An example of the result is shown in FIG. 12, in the form of a curve plotting the number n of image lines as a function of a given direction α plotted along the abscissa. Two maxima at respective abscissa positions $\alpha_1$ and $\alpha_2$ are clearly visible, corresponding respectively to values of about 20° and 110°.

The difference $\alpha_2 - \alpha_1$ between the maxima varies as a function of the state of aging of the skin, tending to decrease with age. Thus, by determining the difference between the maxima, it is possible to obtain information that is helpful in evaluating the of aging of the skin.

Naturally, the invention is not limited to the embodiments given above. In particular, it is possible to use a sensor other than the sensor sold under the trademark Touchchip®.

Throughout the description, including in the claims, the term "comprising a" should be understood as being synonymous with "comprising at least one" unless specified to the contrary.

Although the present invention herein has been described with reference to particular embodiments, it is to be understood that these embodiments are merely illustrative of the principles and applications of the present invention. It is therefore to be understood that modifications may be made to the illustrative embodiments and that other arrangements may be devised without departing from the spirit and scope of the present invention as defined by the appended claims. It is therefore to be understood that, within the scope of the appended claims, the invention may be practiced otherwise than as specifically described herein.

What is claimed as new and desired to be secured by letters patent of the United States is:

1. An apparatus enabling a person to evaluate the hydration of a region of the body with the region including at least one of a region of the skin and a region of mucous membranes, the apparatus comprising:
   a sensor comprising an array of non-optical capacitive detection cells, and
   a processor apparatus arranged to deliver at least water content information in or on the surface of the region based on signals coming from said sensor,
   wherein the sensor presents spatial resolution of at least 100 μm in at least one direction,
   wherein the apparatus is arranged to analyze variation in water content over time with the sensor in place on the region under analysis.

2. An apparatus according to claim 1, wherein the information is delivered in the form of at least one of a visual image, a visual message, and an audio message.

3. An apparatus according to claim 1, wherein the apparatus is arranged to exchange data with at least one of a personal computer and a portable terminal.

4. An apparatus according to claim 3, wherein the apparatus is arranged to exchange data with a mobile telephone.

5. An apparatus according to claim 1, wherein the sensor presents spatial resolution of at least 50 μm in at least one direction.

6. An apparatus according to claim 1, wherein the array is two-dimensional.

7. An apparatus according to claim 1, wherein the apparatus is arranged to deliver at least one image of the region analyzed by the sensor.

8. An apparatus according to claim 7, wherein the processor apparatus is arranged to perform statistical processing of said image, and wherein said information results at least from said statistical processing.

9. An apparatus according to claim 1, wherein the apparatus is arranged to determine information relating to tendency to transpire of an individual under examination based on variation of water content over time.

10. An apparatus according to claim 1, wherein the array of capacitive detection cells occupies an area lying in the range from about 10 mm×10 mm to about 20 mm×20 mm.

11. An apparatus according to claim 1, wherein the sensor comprises more than 200×200 capacitive detection cells.

12. An apparatus according to claim 1, wherein said information comprises an indication relating to uniformity of water content.

13. An apparatus according to claim 12, wherein mean gray levels of subsets of an image of the region analyzed by the sensor image are determined and a value is calculated that is representative of a difference between said mean gray levels.

14. An apparatus according to claim 13, wherein the subsets of the image are non-intersecting.

15. An apparatus according to claim 13, wherein the subsets of the image are disposed in an irregular manner over the image.

16. An apparatus according to claim 1, wherein the apparatus is arranged to enable the sensor to analyze said region for a predefined duration.

17. An apparatus according to claim 16, wherein the predefined duration lies in the range of from about 1 second to about 30 seconds.

18. An apparatus according to claim 16, wherein the predefined duration lies in the range of from about 2 seconds to 10 seconds.

19. An apparatus according to claim 16, wherein the predefined duration lies in the range of from about 3 seconds to 7 seconds.

20. An apparatus according to claim 1, wherein the apparatus is arranged to deliver an indication relating to a state of aging of the skin.

21. An apparatus enabling a person to evaluate the hydration of a region of the body with the region including at least one of a region of the skin and a region of mucous membranes, the apparatus comprising:
   a sensor comprising an array of non-optical capacitive detection cells; and
   a processor apparatus arranged to deliver at least water content information in or on the surface of the region based on signals coming from said sensor,
   wherein the sensor presents spatial resolution of at least 100 μm in at least one direction, wherein the apparatus is arranged to deliver an indication relating to a state of aging of the skin, wherein the processing apparatus is arranged to determine two major directions of skin lines and a difference that exists between said directions, and wherein the apparatus is arranged to deliver an indication relating to the state of aging of the skin from said difference.

22. An apparatus enabling a person to evaluate the hydration of a region of the body with the region including at least one of a region of the skin and a region of mucous membranes, the apparatus comprising:
a sensor comprising an array of non-optical capacitive detection cells; and
a processor apparatus arranged to deliver at least water content information in or on the surface of the region based on signals coming from said sensor,
wherein the sensor presents spatial resolution of at least 100 μm in at least one direction, wherein the apparatus is arranged to deliver at least one image of the region analyzed by the sensor, wherein the processor apparatus is arranged to perform statistical processing of said image, wherein the information results at least from said statistical processing; and wherein the statistical processing comprises determining a gray level shared by a greatest number of pixels in the image.

23. An apparatus enabling a person to evaluate the hydration of a region of the body with the region including at least one of a region of the skin and a region of mucous membranes, the apparatus comprising:
a sensor comprising an array of non-optical capacitive detection cells; and
a processor apparatus arranged to deliver at least water content information in or on the surface of the region based on signals coming from said sensor,
wherein the sensor presents spatial resolution of at least 100 μm in at least one direction, wherein said information comprises an indication relating to uniformity of water content, wherein mean gray levels of subsets of an image of the region analyzed by the sensor image are determined and a value is calculated that is representative of a difference between said mean gray levels, and wherein the value is a standard deviation.

24. An apparatus enabling a person to evaluate the hydration of a region of the body with the region including at least one of a region of the skin and a region of mucous membranes, the apparatus comprising:
a sensor comprising an array of non-optical capacitive detection cells; and
a processor apparatus arranged to deliver at least water content information in or on the surface of the region based on signals coming from said sensor,
wherein the sensor presents spatial resolution of at least 100 μm in at least one direction, wherein said information comprises an indication relating to uniformity of water content, wherein mean gray levels of subsets of an image of the region analyzed by the sensor image are determined and a value is calculated that is representative of a difference between said mean gray levels, and wherein the subsets of the image are formed by a rectangular grid over at least a portion of the image.

25. An apparatus enabling a person to evaluate the hydration of a region of the body with the region including at least one of a region of the skin and a region of mucous membranes, the apparatus comprising:
a sensor comprising an array of non-optical capacitive detection cells; and
a processor apparatus arranged to deliver at least water content information in or on the surface of the region based on signals coming from said sensor,
wherein the sensor presents spatial resolution of at least 100 μm in at least one direction, wherein said information comprises an indication relating to uniformity of water content, wherein mean gray levels of subsets of an image of the region analyzed by the sensor image are determined and a value is calculated that is representative of a difference between said mean gray levels, wherein the subsets of the image are disposed in an irregular manner over the image, and wherein the apparatus is arranged to compare the image with images in a bank of images, and at least on the basis of the comparison, to derive information that is useful for evaluating a state of at least one of the skin and a mucous membrane.

26. An apparatus enabling a person to evaluate the hydration of a region of the body with the region including at least one of a region of the skin and a region of mucous membranes, the apparatus comprising:
a sensor comprising an array of non-optical capacitive detection cells; and
a processor apparatus arranged to deliver at least water content information in or on the surface of the region based on signals coming from said sensor,
wherein the sensor presents spatial resolution of at least 100 μm in at least one direction, wherein the apparatus is arranged to deliver an indication relating to a state of aging of the skin, and wherein the processing apparatus is arranged to determine two major directions of skin lines and a difference that exists between said directions.

27. An apparatus enabling a person to evaluate the hydration of a region of the body with the region including at least one of a region of the skin and a region of mucous membranes, the apparatus comprising:
a sensor comprising an array of non-optical detection cells, and
a processor apparatus arranged to deliver at least one piece of information relating to hydration of the region based on signals coming from said sensor;
the process or apparatus is arranged to determine two major directions of skin lines and a difference that exists between said directions and the apparatus is arranged to deliver an indication relating to the state of aging of the skin from said difference.

* * * * *